US008778308B2

(12) United States Patent
Amoh et al.

(10) Patent No.: US 8,778,308 B2
(45) Date of Patent: Jul. 15, 2014

(54) ANGIOGENSIS MODELS USING NESTIN-EXPRESSING STEM CELLS TO IMAGE NASCENT BLOOD VESSELS

(76) Inventors: Yasuyuki Amoh, San Diego, CA (US); Lingna Li, San Diego, CA (US); Meng Yang, San Diego, CA (US); Ping Jiang, San Diego, CA (US)

(*) Notice: Subject to any disclaimer, the term of this patent is extended or adjusted under 35 U.S.C. 154(b) by 0 days.

(21) Appl. No.: 10/977,219

(22) Filed: Oct. 28, 2004

(65) Prior Publication Data
US 2005/0170330 A1 Aug. 4, 2005

Related U.S. Application Data

(60) Provisional application No. 60/515,291, filed on Oct. 28, 2003.

(51) Int. Cl.
*A61B 5/00* (2006.01)
*G01N 21/64* (2006.01)
*G01N 33/50* (2006.01)

(52) U.S. Cl.
CPC .................................. *G01N 33/5073* (2013.01)
USPC .............. 424/9.6; 435/6.1; 435/354; 435/375

(58) Field of Classification Search
USPC .................................... 800/3, 8, 21; 435/325
See application file for complete search history.

(56) References Cited

U.S. PATENT DOCUMENTS

2003/0077823 A1* 4/2003 Li et al. .......................... 435/366
2005/0019801 A1* 1/2005 Rubin et al. ....................... 435/6

FOREIGN PATENT DOCUMENTS

| WO | WO-01/36482 | 5/2001 |
| WO | WO-03/024406 | 3/2003 |
| WO | WO-03/035879 | 5/2003 |

OTHER PUBLICATIONS

Lyle et al., 1999, Journal of Investigative Dermatology, Symposium Proceedings/the Society for Investigative Dermatology, vol. 4, No. 3, p. 296-301.*
Akiyama et al., 2000, Journal of Investigative Dermatology, vol. 114, No. 2, p. 321-327.*
Turksen, K., 2004, Developmental Cell, vol. 6, No. 4, p. 454-456.*
Murray et al. (1999) Genetic modification of animals in the next century. Theriogenoogy. 51:149-159.*
Sigmund, C., Jun. 2000, Arterioscler. Thromb. Vasc. Biol., p. 1425-1429.*
Houdebine, L-M., 2002, Journal of Biotechnology, vol. 98, p. 145-160.*
Gojo et al. (2000) Gene therapy and Transplantation. Transplantation. 69:1995-1999.*
Leiter et al. (2002) Mice with targeted gene disruptions or gene insertions for diabetes research:problems, pitfalls, and potential solutions. Diabetologia 45:296-308.*
Kolb et al. (1999) Insertion of a foriegn gene into the beta-casein locus by Cre-mediated site-specific recombination. Gene 227:21-31.*
Houdebine. (2000) Transgenic animal bioreactors. Transgenic Research. 9:305-320.*
Definition of angiogenesis from online Merriam-Webster dictionary, http://www.m-w.com/, one page provided.*
Cao et al., Adenovirus mediated gene transfer to skeletal muscle, Microsc Res Tech. 58(1):45-51, 2002.*
Gordan et al., Universal tumor antigens as targets for immunotherapy. Cytotherapy, 4(4):317-27, 2002.*
Thaler et al., The cytoplasmic structure hypothesis for ribosome assembly, vertical inheritance, and phylogeny, Bioessays, 31(7):774-83, 2009.*
Rosenberg et al. Cellular basis of skin allograft rejection: an in vivo model of immune-mediated tissue destruction. Annu Rev Immunol. 10: 333-58, 1992.*
Fabre, Epidermal allografts. Immunol Lett. 29(1-2): 161-5, 1991.*
Kadonaga, The DPE, a core promoter element for transcription by RNA polymerase II, Exp Mol Med. 34(4):259-64, 2002.*
Kornberg, The molecular basis of eukaryotic transcription. Proc Natl Acad Sci U S A. 104(32): 12955-61, 2007.*
Brembeck et al The tissue-dependent keratin 19 gene transcription is regulated by GKLF/KLF4 and Sp1, J Biol Chem. 275(36):28230-9, 2000.*
Castex-Rizzi et al., Annales de Dermatologie et de Venerologie (2002) 129(5):783-786.
Filippov et al., Molecular and Cellular Neuroscience (2003) 23(3):373-382.
Klein et al., The Journal of Histochemistry and Cytochemistry (2003) 51(6):697-706.
Lu et al., Society for Neuroscience Abstract Viewer and Itinerary Planner (2002) abstract No. 34.10.
Mokry et al., Folia Biologica (1998) 44(5):155-161.
Mokry et al., General Physiology and Biophysics (1999) 18(1):25-29.
Sugawara et al., Laboratory Investigation (2002) 82(3):345-351.
Supplementary European Search Report for EP 04796816.9, mailed Aug. 16, 2007, 6 pages.
Amoh et al., PNAS USA (2004) 101:13291-13295.
Croix et al., Science (2000) 289:1197-1202.
Dahlstrand et al., Cancer Res. (1992) 52:5334-5341.
Eliasson et al., J. Biol. Chem. (1999) 274:23996-24006.
Kurihara et al:, Gene Ther. (2000) 7:686-693.

(Continued)

*Primary Examiner* — Deborah Crouch
*Assistant Examiner* — Titilayo Moloye

(57) ABSTRACT

The disclosed invention relates to the observation that nestin expression is a marker for endothelial cell proliferation. Nestin expression is particularly useful as a marker for angiogenesis, particularly for tumor-related angiogenesis. Specifically, nestin serves as an excellent endothelium marker for brain tumors such as gliomas, hemangioblastomas, Schwannomas, medulloblastomas, and meningiomas. Accordingly, the disclosed invention relates to the use of this marker as a basis to model angiogenic activity.

10 Claims, 7 Drawing Sheets

(56) References Cited

OTHER PUBLICATIONS

Lendahl et al., Cell (1990) 60:585-595.
Lingna Li et al., PNAS USA (2003) 100:9958-9961.
Lothian and Lendahl, Eur. J. Neurosci. (1997) 9:452-462.
Messam et al., Exp. Neurol. (2000) 161:585-596.
Rutka et al., Int. J. Dev. Neurosci. (1999) 17:503-515.
Tohyama et al., Am. J. Pathol. (1993) 143:258-268.
Tohyama et al., Lab. Invest. (1992) 66:303-313.
Zimmerman et al., Neuron (1994) 12:11-24.
International Search Report for PCT/US04/36105, mailed on Jun. 8, 2005, 2 pages.
Lardon et al., Histochemistry and Cell Biology (2002) 117:535-540.
Oshima et al., Cell (2001) 104:233-245.
Taylor et al., Cell (2000) 102:451-461.

* cited by examiner

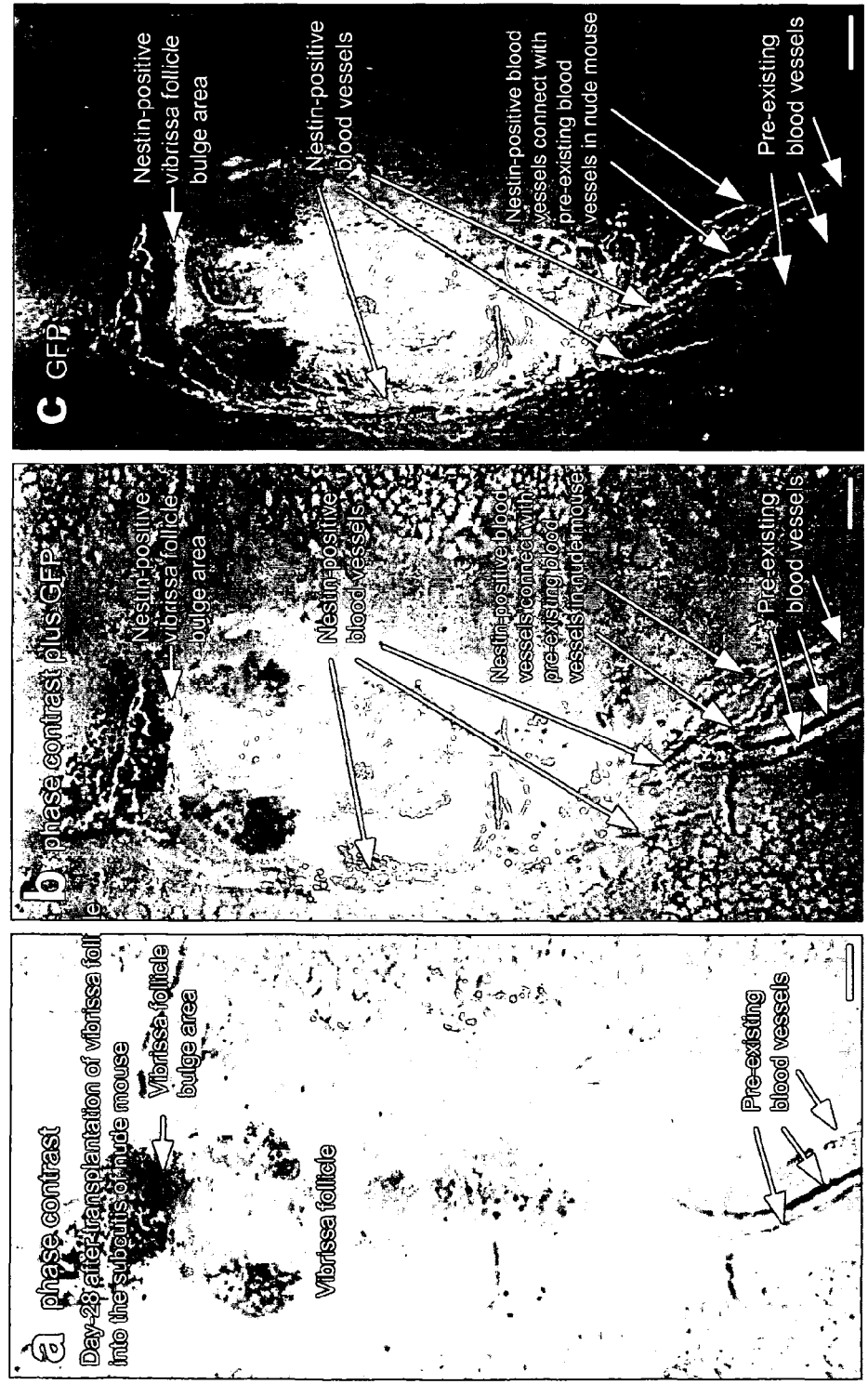
Fig. 2 a-c

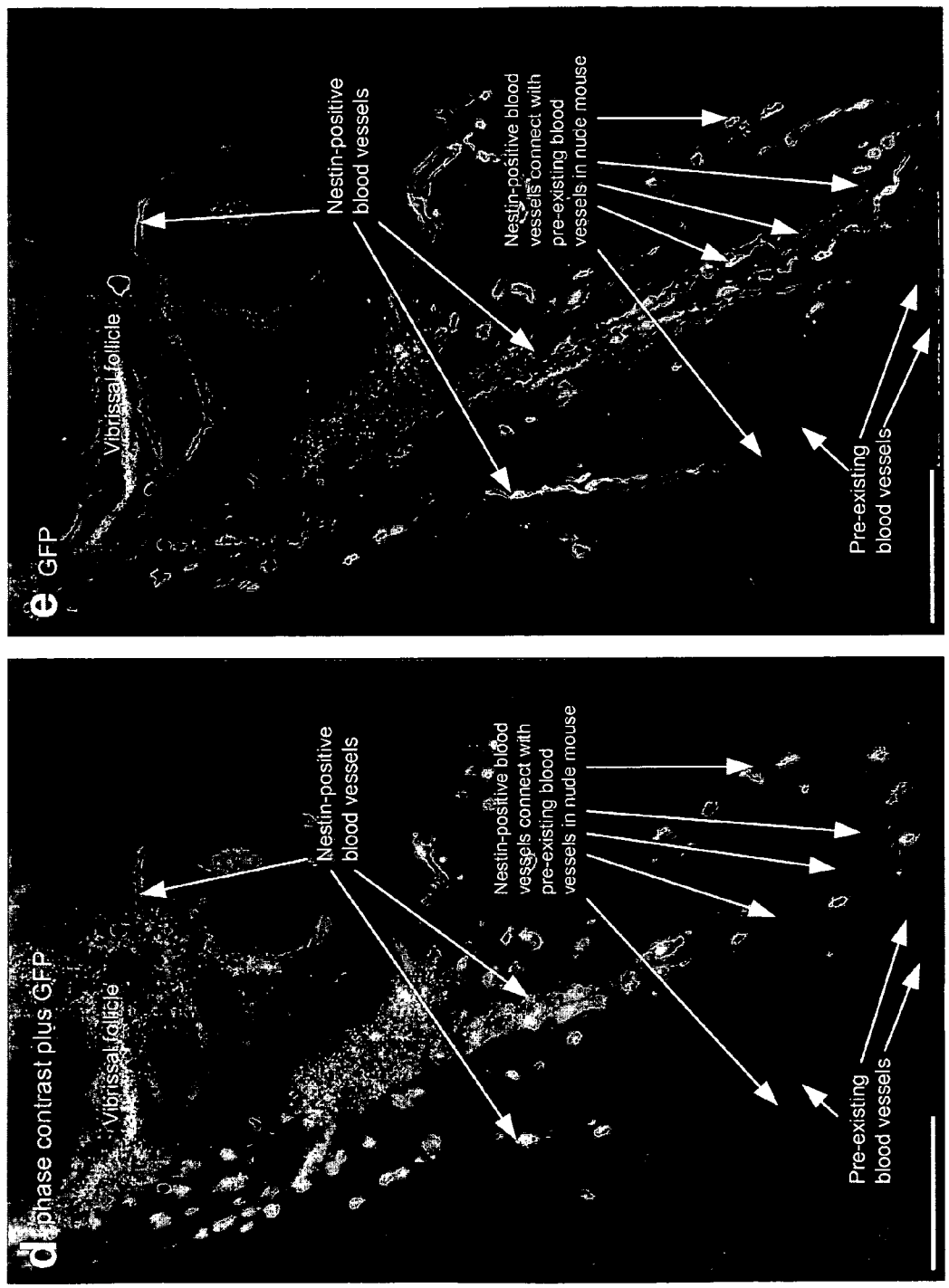
Fig. 2 d-e

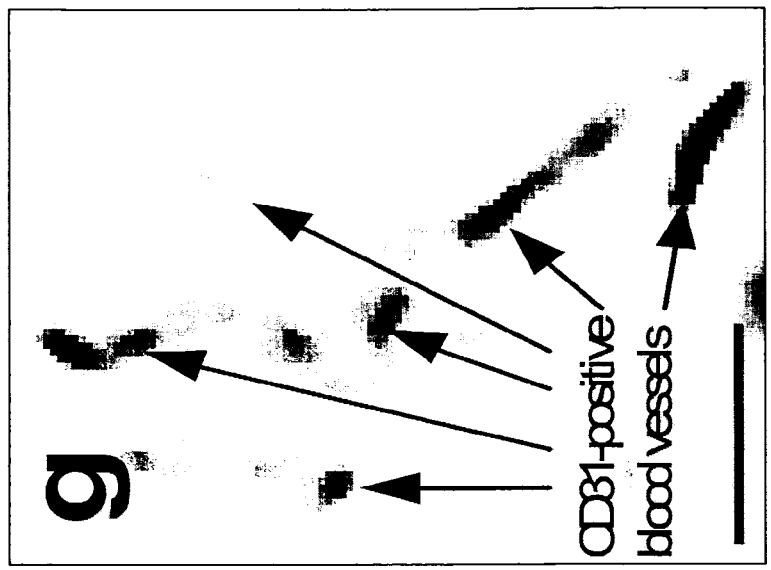
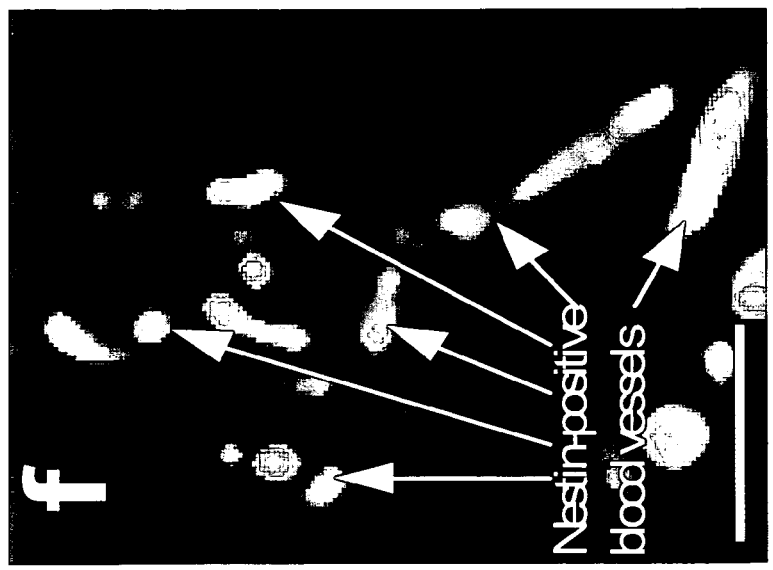
Fig. 2 f-g

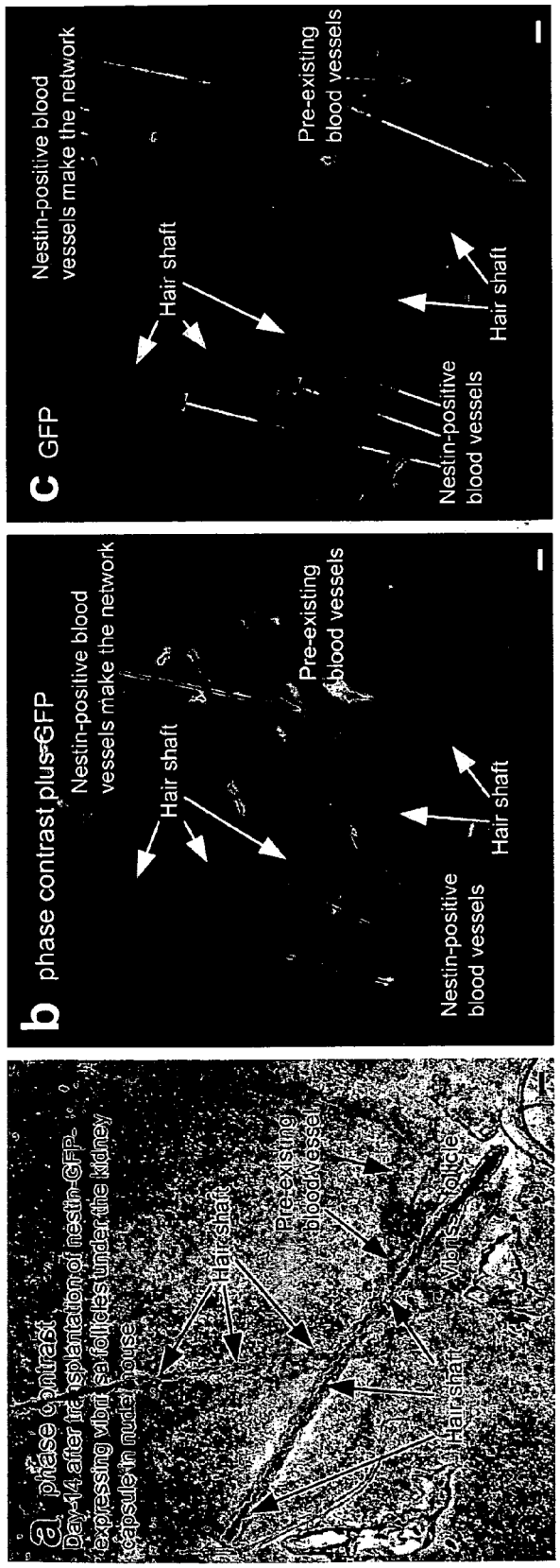
Fig. 3 a-c

Fig. 4 a-d
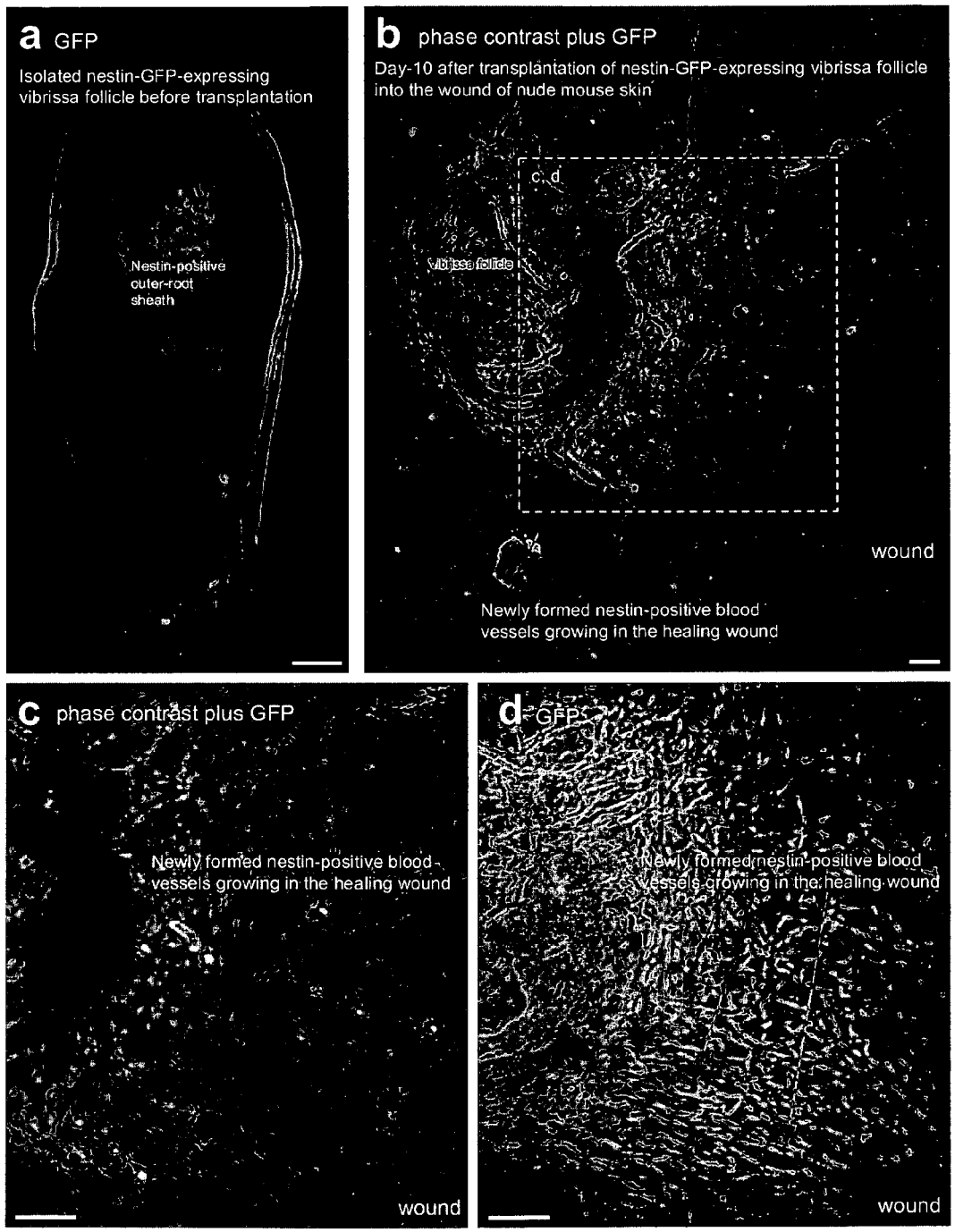

ANGIOGENSIS MODELS USING NESTIN-EXPRESSING STEM CELLS TO IMAGE NASCENT BLOOD VESSELS

CROSS-REFERENCE TO RELATED APPLICATION

This application claims benefit of U.S. provisional application 60/515,291 filed 28 Oct. 2003. The contents of which are incorporated herein by reference in their entirety.

TECHNICAL FIELD

The disclosed invention relates to the observation that nestin expression is a marker for endothelial cell proliferation. Nestin expression is particularly useful as a marker for angiogenesis, particularly for tumor-related angiogenesis. Specifically, nestin serves as an excellent endothelium marker for brain tumors such as gliomas, hemangioblastomas, Schwannomas, medulloblastomas, and meningiomas.

BACKGROUND ART

Nestin is one of the intermediate filaments, together with vimentin and glial fibrillary acidic protein (GFAP), and is detected abundantly in neuroepithelial stem/progenitor cells in the growing central nervous system of embryonal rats and humans (Lendahl, U., et al., *Cell* (1990) 60: 585-595; Messam, C. A., et al., *Exp. Neurol.* (2000) 161: 585-596; Tohyama, T., et al., *Lab. Invest.* (1992) 66: 303-313; Tohyama, T, et al., *Am. J. Pathol.* (1993) 143: 258-268)). Nestin forms intermediate filament bundles, perhaps with vimentin, by copolymerization in neuroepithelial cells (Eliasson, C., et al., *J. Biol. Chem.* (1999) 274: 23996-24006; Rutka, J. T., et al., *Int. J. Dev. Neurosci.* (1999) 17: 503-515).

Nestin mRNA is expressed highly in the cerebrum of developing rat embryos at embryonic day 15 (E15), declines toward postnatal day 12 (P12), and disappears from P18 to the adult stage (Lendahl, U., et al., supra). Using nestin transgene-promoted β-galactosidase expression analysis in mice, LacZ activity has been detected in the neuroepithelium and somites shortly after neural tube closure (E9) (Zimmerman, L., et al., *Neuron* (1994) 12: 11-24). The LacZ staining becomes stronger in the proliferative ventricular zones of the mouse embryonic striatum and cerebral cortex at E14.5 and E16.5 and decreases in expression in the adult cortex, becoming restricted to a population of ependymal cells.

Substantial nestin expression has also been detected in human gliomas and glioblastomas (Dahlstrand, J., et al., *Cancer Res* (1992) 52: 5334-5341). Nestin immunostaining has frequently been observed in highly malignant gliomas, especially glioblastomas, as compared with the less malignant forms such as pilocytic astrocytomas. In contrast, nestin is rarely detected by immunostaining in non-neoplastic brain tissues, occurring sometimes faintly in vascular endothelial cells.

Nestin mRNA is approximately 6.2 kilobases long, and its gene contains three introns. Interestingly, neuroepithelium-specific nestin expression is driven by the second intron of the nestin gene, whereas muscle precursor-specific expression is driven by the first intron (Lothian, C., et al., *Eur. J. Neurosci.* (1997) 9: 452-462; Zimmerman, L, et al., supra).

Nestin expression was previously examined in seven human glioma/glioblastoma-derived culture cell lines (Kurihara, H., et al., *Gene Ther.* (2000) 7: 686-693). The level of expression varied from high (U251, KG-1C) to non-detectable (NP-2, LN-Z308, T98G) according to Northern blot analysis. The expression levels did not parallel the growth rates of the cell lines, although the degree of malignancy generally reflects tumor doubling time in vivo. The neuronal cell-specific regulator, consisting of the second intron before the 5' upstream region of the gene, drove LacZ expression in parallel with the extent of mRNA expression in each cell line (Kurihara, H., et al., supra). This variability in nestin expression levels in the glioma/glioblastoma cell lines caused the reevaluation of nestin expression in human glioma/glioblastomas from low to high malignancy grades.

Although a number of angiogenesis-related genes are reported in colorectal cancer endothelium, the nestin gene is not included in the list (Croix, B. S., et al., *Science* (2000) 289: 1197-1202). Angiogenesis-related genes in brain tumor endothelium may be different from those in colorectal endothelium. It is noteworthy that strong nestin expression is found in brain tumor endothelium even if no nestin expression is found in the brain tumor cells.

SUMMARY OF THE INVENTION

Nestin-expressing cells, marked by a fluorescent protein (FP) proliferated in the epidermis and dermis of the regenerating skin, reflecting a population of nestin positive cells, which proliferates and migrates from the bulge area close to the site of lesion in response to injury. Nestin expression is particularly useful as a marker for tumor-related angiogenesis. Specifically, nestin serves as an excellent endothelium marker for brain tumors such as gliomas, hemangioblastomas, Schwannomas, medulloblastomas, and meningiomas. Accordingly, the described invention has utility as a model for angiogenesis.

In a preferred embodiment, the disclosed invention relates to a method of monitoring blood vessel development, comprising providing an angiogenic stem cell, wherein the stem cell comprises an expression cassette encoding a fluorescent protein (FP) under genetic control of a nestin regulatory element; culturing the stem cell in a host; and monitoring angiogenic activity of the stem cell that leads to blood vessel development.

In one aspect of the invention, the angiogenic stem cell is a nestin expressing cell, such as a hair follicle cell or a tumor cell. The cells can be grown in vitro or in vivo. Examples of tumor cells include melanomas, gliomas, hemangioblastomas, Schwannomas, medulloblastomas, and meningiomas.

Another aspect of the invention utilizes one or more fluorescent proteins under control of a nesting regulatory element. Examples of these proteins include green fluorescent protein (GFP), red fluorescent protein (RFP), blue fluorescent protein (BFP) and yellow fluorescent protein (YFP). Preferably, the nestin regulatory element is encoded by the second intron of the human nestin gene.

In another aspect of the disclosed invention involves the use of a host organism. The host organism is preferably a vertebrate organism. Particularly preferred host organisms are mammalian or avian hosts. Examples of preferred mammalian hosts include mice, rats, rabbits, dogs and cats. Examples of preferred avian hosts include chickens and chicken eggs.

In one embodiment of the disclosed invention, an angiogenic stem cells comprises a first FP protein under nestin regulatory control and the host organism comprises a second FP protein under nestin regulatory control, wherein the first FP protein is different from the second FP protein.

Another embodiment of the disclosed invention relates to a method of screening for a modulator of angiogenesis, comprising providing an angiogenic stem cell, wherein the stem cell comprises an expression cassette encoding a fluorescent protein (FP) under genetic control of a nestin regulatory element; culturing the stem cell in a host in the presence of an angiogenesis modulating agent; and monitoring angiogenic activity of the stem cell.

BRIEF DESCRIPTION OF THE DRAWINGS

FIG. 2A-G shows images of ND-GFP vibrissa follicles transplanted into the subcutis of a nude mouse (scale bars, 100 μm).

FIG. 3A-C show images of transplanted ND-GFP vibrissa follicles under the kidney capsule of a nude mouse (scale bars, 100 μm).

FIG. 4A-E show images and a schematic of an isolated ND-GFP vibrissa follicle before transplantation, transplanted into a wounded nude-mouse skin 10 days after transplantation, higher magnifications of the area in FIG. 4B (Scale bars, 100 μm).

MODES OF CARRYING OUT THE INVENTION

Figure 1:
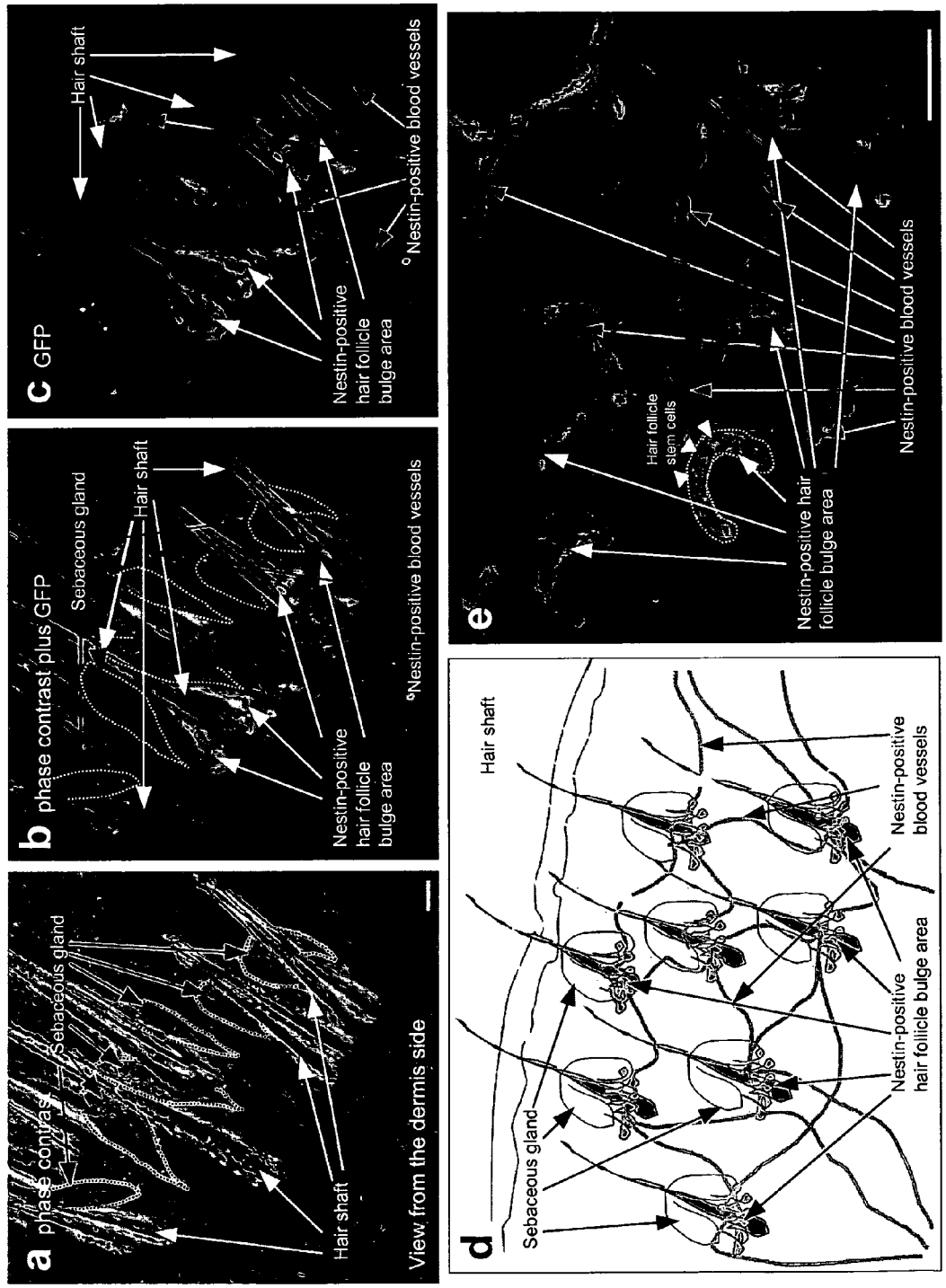
FIG. 1A-E shows views from the dermis side of the doral skin in the ND-GFP transgenic mice. Scale bars in the figures represent a distance of 100 μm.

The disclosed invention provides model systems for the study of angiogenesis. In a preferred embodiment, angiogenic endothelial stem cells are labeled with an expression system encoding a fluorescent protein, the expression of which is governed by regulatory sequences from a gene that is disclosed as being preferentially expressed in angiogenic endothelial stem cells. The expression system provides a visual marker with which to observe the angiogenic process. Nestin-expressing cells are disclosed here as a source of angiogenic endothelial stem cells and nestin regulatory elements are preferably used to control expression of the marker protein. Accordingly, the disclosed model systems use angiogenic endothelial stem cells encoding one or more fluorescent proteins under the control of nestin regulatory sequences to model angiogenesis.

Angiogenic Stem Cells

The disclosed model system uses labeled progenitor or stem cells as a marker for angiogenesis. Nestin expression is an excellent marker for stem cells, such as central nervous system (CNS) stem cells, neuroepithelial stem cells and hair follicle sheath progenitor cells. Nestin is also an excellent marker of certain cancer cells such as melanoma and particular brain tumors such as gliomas, hemangioblastomas, Schwannomas, medulloblastomas and meningiomas.

Nestin is an intermediate filament that is a marker for central nervous system progenitor cells. In particular, transgenic mice with green fluorescent protein (GFP) under the control of the nestin regulatory sequences have been generated and used for visualization of the self-renewal and multipotency of CNS stem cells. Although, in a preferred embodiment, the nestin may be linked to a detection agent such as green fluorescent protein to facilitate the isolation process, it is contemplated that other markers for these cells can be used to isolate the hair follicle stem cells as well any other detectable agents. For example, cells can be assayed in vitro or in situ and tested for a labeled binding partner, antibody, or nucleic acid that binds. In embodiments where the hair follicle stem cell is attached to a solid support, assays may employ other types of signal molecules, where unbound signal molecule can be separated from signal molecule bound to the cell. For example, a signal molecule may be labeled with a radioactive isotope (e.g., $^{125}I$, $^{131}I$, $^{35}S$, $^{32}P$, $^{14}C$ or $^3H$); a light scattering label (Genicon Sciences Corporation, San Diego, Calif. and see, e.g., U.S. Pat. No. 6,214,560); an enzymatic or protein label (e.g., a fluorescent protein (FP) or peroxidase); or another chromogenic label or dye (e.g., Texas Red). In addition, FACS or other cell sorting mechanism may be used to isolate cells.

The location of hair follicle stem cells varies depending on the hair-cycle. In early anagen in nestin-FP transgenic mice, nestin-expressing cells are located in the permanent upper hair follicle right below the sebaceous glands in the follicle bulge where the hair follicle stem cells are located. The nestin-expressing cells in the bulge area are relatively small, oval shaped and surround the hair shaft with short dendrites connecting them to each other. FIG. 3 shows that the location of the nestin-expressing cells in the hair follicle are hair-cycle dependent. During telogen and early anagen, the Fluorescent protein-positive cells, i.e., nestin-expressing cells, are mainly in the bulge area. Fluorescent protein-expressing hair follicle stem cells are seen in both telogen and early anagen. As the hair follicle stem cells from telogen appear to be the most primitive and are localized, they are preferred for harvesting, although the cells may be harvested from any stage of the hair-cycle. Techniques for harvesting are discussed in the U.S. patent application Ser. No. 10/251,657, entitled "Nestin-expressing hair follicle stem cells," which is hereby incorporated by reference.

In mid and late anagen, the FP-expressing cells are located in the upper outer root sheath as well as in the bulge area but not in the hair matrix bulb. These observations suggest that the nestin-expressing cells form the outer-root sheath consistent with behavior observed for hair follicle stem cells. Results of the immunohistochemical staining showed revealed that nestin, FP, keratin 5/8 and keratin 15 co-localized in the hair follicle bulge cells, outer root sheath cells and basal cells of the sebaceous glands. These data further demonstrated that nestin-FP expressing cells in the hair follicle bulge are hair follicle stem cells. Nestin-driven GFP was also found to be highly expressed in an interfollicular neural-like network. The common expression of nestin in neural stem cells, in hair follicle stem cells, and in an inter-hair-follicle neural-like network suggests their common origin.

In typical use, labeled cells are introduced into a host organism, where the cells grow and differentiate to form nascent blood vessels. The nascent vessels typically anastomose with existing vessels in the host organism. Labeled cells are implanted in any suitable host and allowed to progress and develop using standard methods of implantation such as grafting, transcutaneous injection and implantation.

The implantation can be performed in any manner known in the art. In one embodiment, the hair follicle stem cells or differentiated cells derived therefrom are systemically injected into the subject. In another aspect, the hair follicle stem cells or differentiated cells derived therefrom are injected directly into an organ or tissue of the subject. Preferably the organ or tissue is the retinal, brain, liver or an organ or muscle associated with the cardiovascular system, such as the heart or lung. In addition, cells or tissues adhered or grown on synthetic supports which are then implanted are also contemplated. The hair follicle stem cells or differentiated cells derived therefrom can be transplanted heterologously in a different subject than the subject from which the cells were derived. However, due to the accessibility of the hair follicle stem cells, in one preferred embodiment the cells can be obtained from the subject to be treated and if desired, grown to provide differentiated cells, and then either the stem cells or differentiated cells may be transplanted autologously. The use of hair follicle stem cell banks is also contemplated as the stem cells of the invention are sufficiently primitive and thus the host will not likely reject the cells when transplanted.

Techniques for implantation of the labeled cells into vertebrates include direct implantation by surgical orthotopic implantation (SOI) at the desired site. Implantation in the kidney capsule is a preferred site of implantation. When the labeled cells are tumor cells, the site of implantation is typically the site from which the tumor cells were derived. Suitable sites include lung, liver, pancreas, stomach, breast, ovary, prostate, bone marrow, brain, and other tissues susceptible to malignancy. Once the labeled cells have been implanted, the vertebrate becomes a model system for studying angiogenesis. The labeled cells are then allowed to progress and develop and the vertebrate is monitored for appearance of the FP labeled cells at sites distal from the original implantation site. The monitoring can occur either on the whole vertebrate by direct observation, such as with a fluorescent microscope, or the tissues may be excised and examined microscopically.

Suitable vertebrate subjects for use as models are preferably mammalian subjects, most preferably convenient laboratory animals such as rabbits, rats, mice, dogs, cats and the like. For closer analogy to human subjects, primates could also be used. Particularly useful are subjects that are particularly susceptible to tumor development, such as subjects with impaired immune systems, typically nude mice or SCID mice. Any appropriate vertebrate subject can be used, the choice being dictated mainly by convenience and similarity to the system of ultimate interest. In vitro systems such as tissue culture can also be used as a suitable host. Suitable systems for such study include solid supported cultures such as those maintained on collagen gels and the like.

Labeled cells can be prepared in vitro using standard direct gene transfer methods or in vivo by harvesting labeled cells from a transgenic host. Direct gene transfer methods include the use of liposomes, calcium phosphate precipitation, electroporation and gene gun. Lipofection is preferred. For example, labeled cancer cells are preferably prepared using a retroviral vector encoding a fluorescent protein or other label under control of nestin regulatory elements. Fluorescent protein labeled hair follicle stem cells are preferably harvested from a transgenic animal source. Regulatory elements of nestin expression are used to differentially drive expression of a fluorescent protein coding sequence in angiogenic stem cells, thus making the labeled stems cells markers for angiogenesis.

Fluorescent Proteins

The model generally involves producing one or more fluorescent protein-labeled cells. The fluorescent protein-labeled cells are produced by introducing an expression system into a host cell, where the expression system comprises a fluorescent protein under the control of one or more nestin regulatory sequences. In a preferred embodiment, a vertebrate host organism, preferably a mammalian or avian host, is modified to contain one or more of the fluorescent protein-labeled cells. These cells are cultured or allowed to grow within the host organism.

A variety of fluorescent proteins have been used as labels for a number of years. The originally isolated protein emitted green wavelengths and came to be called green fluorescent protein (GFP). Because of this, green fluorescent protein became a generic label for such fluorescent proteins in general, although proteins of various colors including red fluorescent protein (RFP), blue fluorescent protein (BFP) and yellow fluorescent protein (YFP) among others have been prepared. The nature of these proteins is discussed in, for example, U.S. Pat. Nos. 6,232,523; 6,235,967; 6,235,968; and 6,251,384 all incorporated herein by reference. These patents describe the use of fluorescent proteins of various colors to monitor cell growth and tumor metastasis in transgenic rodents. In addition, these fluorescent proteins have been used to monitor expression mediated by promoters in U.S. application Ser. No. 09/812,710; to monitor infection by bacteria in U.S. application Ser. No. 10/192,740 and to monitor cell sorting in U.S. Provisional Application No. 60/425,776. The use of fluorescent proteins of different colors to label the nucleus and cytoplasm of cells is disclosed in U.S. Provisional Application Nos. 60/404,005 and 60/427,604 and mice which are labeled in all tissues, and thus have a consistent fluorescent of the same color are described in U.S. Provisional Application No. 60/445,583. All of these documents are incorporated herein by reference.

Nestin

Nestin is an intermediate filament gene that is a marker for progenitor or stem cells. (*Homo sapiens* nestin (NES), mRNA (NM_006617).) Nestin expression distinguishes the stem cells from the more differentiated cells. Neuroepithelial stem cells express nestin and down-regulate it sharply when they differentiate from proliferating stem cell to postmitotic neuron. (Lendahl, et al., (1990) Cell 60: 585-595.) Nestin is also expressed in muscle precursors but not in mature muscle cells. Independent cell type-specific elements in the first and second introns of the nestin gene consistently directed reporter gene expression to developing muscle and neural precursors, respectively in transgenic animals. The second nestin intron contains an enhancer that functions in CNS stem cells. (Zimmerman, et al., (1994) Neuron 12: 11-24; (*Homo sapiens* nestin gene, intron 2 (AF004335).) The identification of these elements facilitates analysis of mechanisms controlling the switch in gene expression that occurs when certain progenitor or stems terminally differentiate.

The following examples are intended to illustrate and do not in anyway limit the scope of the disclosed invention.

Example 1

Proliferating Epithelial Cells Express Nestin

Proliferating epithelial cells express nestin as illustrated by high levels of nestin expressed in bovine aortic endothelial cells in static culture. Bovine aortic endothelial cells (BAECs) were used in the example discussed below to examine endothelial nestin expression.

Endothelial cells proliferate by cell division in static culture, whereas proliferation decreases under physiologic laminar flow (approximately 15 dyn/cm$^2$) (Malek, A. M., et al., *JAMA* (1999) 282: 2035-2042). Nestin was expressed strongly in BAECs in a static culture by both Northern blot analysis and immunostaining. To examine whether the nestin expression was proliferation dependent, BAECs were subjected to a shear stress flow of 15 dyn/cm$^2$ for 12 hours.

Bovine aortic endothelial cells (BAECs) scraped off the inner surface of the bovine thoracic aortas using a razor blade were used in the following experiment. The BAECs were then cultured in 6-well plates in RPMI 1640 with 20% fetal bovine serum. When BAECs formed a colony of 3 to 6 mm in diameter, the cells were moved to new 6-well plates, where fetal bovine serum was decreased to 10%. Culture cell lines growing in a cobble stone-like sheet formation were selected by 7 to 12 passages and stored in liquid nitrogen until use.

BAECs were cultured on 0.5-mm-thick quartz cover glass. The cover glass was inverted and placed on a parallel plate-type flow chamber (inner space size: 16 mm wide×0.35 mm long×200 μm deep), as described previously (Negishi, Y., et al., *Arterioscler. Thromb. Vasc. Biol.* (2001) 21: 785-790). The apparatus was placed in a $CO_2$ incubator at 37° C. The shear stress forces were calculated based on an equation described previously (Negishi, Y., et al., supra). The flow rate was adjusted to 15 dyn/cm$^2$, which is comparable to the physiologic flow rate.

The BAECs were then fixed in 4% paraformaldehyde in 0.1 M phosphate buffer, pH 7.4, for 24 hours (tissues) or 1 hour (culture cells). BAECs were treated with 50 mM NH4CL in PBS to quench any free aldehyde, then made permeable by 0.1% saponin and 0.4% bovine serum albumin before the primary antibody incubation. The BAECs were first incubated with the primary antibody to nestin at a dilution of 1:5000. For BAECs, the secondary antibody used was indodicarbocyanide-conjugated affinity-purified donkey anti-rabbit IgG (red colored) (Jackson ImmunoResearch, West Grove, Pa.). The nucleus was counterstained blue with 4,6-diamidino-2-phenylindole.

For Northern blot analysis, total RNA was extracted from BAECs, denatured with 6.3% formaldehyde/50% formamide, electrophoresed on a 1.0% agarose gel containing 6.6% formaldehyde, then blotted to a nylon membrane (Amersham Life Science, Tokyo, Japan). Hybridization was performed with a probe of human nestin DNA fragment (560 bp), labeled with -32P deoxy-CTP by a random priming procedure. A glyceraldehyde-3-phosphate dehydrogenase probe was used as a control.

For Western blotting, U251 human glioblastoma cells were solubilized for cell lysates in lysis buffer (70 mM Tris-HCl, pH 6.8, 11.2% glycerol, 3% SDS, 0.01% bromophenol blue, 5% 2-mercaptoethanol). The cell lysates were then subjected to electrophoresis on a 7.5% polyacrylamide gel under a reducing condition, then blotted onto a nitrocellulose membrane for probing with rabbit anti-human nestin antiserum at a dilution of 1:7500. Nestin blots were detected utilizing an ECL detection system (Amersham, Buckinghamshire, United Kingdom).

Expression of nestin mRNA diminished significantly with shear stress flow by Northern blot analysis. Furthermore, a flow-dependent decrease of nestin expression was confirmed by immunostaining.

Example 2

Nestin Immunostaining for Brain Tumors

Polyclonal antibodies to nestin were raised in rabbits by injecting the synthetic oligopeptide covering the C-terminal 17 amino acids of the human nestin sequence. This antibody reacted with proteins of 210 to 240 kD from U251 cell extracts by Western blotting, as reported previously (Messam, C. A., et al., supra; Tohyama, T., et al., supra (1992)). The immunoblot resembled doublets, perhaps because of the difference in carbohydrate modification, as reported previously (Messam, C. A., et al., supra). The immunoblot disappeared when the synthetic oligopeptide was added to the U251 cell lysate, indicating that the immunoblot represents the nestin protein.

The cross-reactivity of this antibody was further tested with other intermediate filaments including vimentin, GFAP, keratins, and desmin. The antibody to human vimentin showed a single band at a little beyond the 50-kD marker position with both U251 and HeLa cell extracts. The antibody to GFAP displayed an approximately 50-kD band with U251 cell extract, but not with HeLa cell extract. Pooled mouse monoclonal antibodies, anti-cytokeratin AE1/AE3, which recognize a broad subfamily of acidic and basic keratins were used for detecting keratins. The anti-cytokeratin AE1/AE3 recognized an approximately 50-kD protein from HeLa cell extract, but faintly from U251 cell extract. The antibody to human desmin did not display bands with either U251 or HeLa cell extract. Nonimmune rabbit serum did not show any artifactual bands with either U251 or HeLa cell extract. Thus, the antibody to nestin displayed large-sized bands corresponding to nestin molecular-sized proteins reported previously (Messam, C. A., et al., supra; Tohyama, T., et al., supra (1992)) but did not cross-react with other intermediate filaments.

Seventy-one (71) brain tumor samples were then immunostained with this antibody. The 71 human brain tumor samples including 57 gliomas and 14 other brain tumors. The gliomas included 6 World Health Organization (WHO) grade I tumors, 11 grade II tumors, 18 grade III tumors, and 22 grade IV tumors. Other brain tumors included four hemangioblastomas, two medulloblastomas, one atypical teratoid/rhabdoid tumor, three meningiomas, two atypical meningiomas, and two Schwannomas. All 71 brain tumors were resected at the Department of Neurosurgery, Gunma University School of Medicine. The diagnoses were established by routine pathologic examinations according to the revised WHO classification at the Department of Pathology, Gunma University School of Medicine.

The human brain and tumor tissues were fixed in 4% paraformaldehyde in 0.1 M phosphate buffer, pH 7.4, for 24 hours (tissues) or 1 hour (culture cells). Small pieces of the tissue sample were embedded in optimal cutting temperature compound for microtome sectioning. The tissue sections were first incubated with the primary antibody to nestin at a dilution of 1:5000. For brain and tumor tissues, an LSAB2/HRP staining kit (DAKO) was used as the secondary antibody reaction system. The procedure consists of a secondary antibody reaction followed by an enzyme reaction with a horseradish peroxidase-labeled streptavidin system. In the enzyme reaction, the peroxidase catalyzes 3-amino-9-ethylcarbazole to an insoluble brown-colored product.

Normal brain cortex tissues were not immunostained with this antibody, although a few vascular endothelial cells showed occasional faint staining, as described previously (Dahlstrand, J., et al., supra). In the glioblastomas (WHO grade IV), the typical nestin staining was fibrillar distribution along the processes of the tumor cells. The staining intensity was classified as 4+ in this tumor. Nestin staining was also evident as a button-like cluster in the cytoplasm of round-shaped tumor cells, (anaplastic oligoastrocytoma, staining intensity is 3+). In some grade III and grade IV gliomas, the staining was limited to proliferative endothelium, (glioblastoma, grade IV) (anaplastic oligodendroglioma, grade III). In the low-grade gliomas, the staining was weak to negligible in a considerable number of tumors, but distinct staining was noted along the endothelium in the tumor, (oligodendroglioma, grade II). This tendency was more marked in other types of brain tumors (Schwannoma and meningioma), whose epithelium immunostained strongly positive for nestin while the tumor cells did not stain at all. Thus, the tumor endothelial cells expressed nestin without regard to the WHO grade for malignancy.

Example 3

Nestin Expression in Hemangioblastomas

Because nestin was expressed in proliferating endothelial cells, it was suspected that it is expressed even in hemangioblastomas because hemangioblasts are thought to be a precursor for both hematopoietic cells and angioblasts (Eichmann, A., et al., *Proc. Natl. Acad. Sci. USA* (1997) 94: 5141-5146). To examine this issue, four human hemangioblastomas were tested. An endothelial cell marker, von Willebrand factor, positively immunostained along endothelium and microcapillary vessels in the hemangioblastoma (Böhling, T., et al., IARC Press (2000), Lyon, France, 223-226).

Nestin also immunostained mostly in microcapillary vessels in the hemangioblastoma. However, typical endothelium consisting of thin cytoplasm with a convex-shaped nucleus was not positive for nestin staining. Because the appearance of endothelium is similar to normal vessels, this type of endothelium may have been well-differentiated and lost nestin expression. Nestin-positive cells consisting of hemangioblastomas may reflect genuine transformed hemangioblasts. Thus, nestin is a marker protein not only for neuroepithelial stem cells and glioma cells but also for hemangioblasts and proliferating endothelial cells.

Example 4

Nestin Immunostaining in Hemangioblastomas

Intermediate Filament Protein, Nestin, Marks Progenitor Cells of the CNS.

Progenitor CNS stem cells are selectively labeled by placing GFP under the control of the nestin regulatory sequences. It was previously demonstrated that during early anagen or growth phase of the hair follicle, nestin-expressing cells, marked by GFP fluorescent in nestin-GFP transgenic mice, appear in the permanent upper hair follicle immediately below the sebaceous glands in the follicle bulge. This is where stem cells for the hair follicle outer-root sheath are thought to be located. The relatively small, oval-shaped, nestin-expressing cells in the bulge area surround the hair shaft and are interconnected by short dendrites. The precise locations of the nestin-expressing cells in the hair follicle vary with the hair cycle.

These observations show that the nestin-expressing cells work for the regeneration of the skin. These data indicate that nestin-expressing cells, marked by GFP, in the hair follicle bulge are indeed progenitors of not only the follicle outer-root sheath but also epidermis.

Several different models of skin wound are currently used and each simulates different aspects of the clinical condition and to varying degrees of accuracy. Nestin-GFP expression of skin wound at 1, 3, 5, 7 and 9 days was determined after punch biopsy injury. Nestin expressing cells were more widespread in the dermis and basal layers in the epidermis at 5 days. Increases in nestin GFP expressing cells were detected by 3 day, reaching maximal immunointensity at 5-9 days after injury.

Recently, Taylor, G., et al., *Cell* (2000) 102: 451-461 reported that hair follicle bulge stem cells are potentially bipotent because they can give rise to not only cells of the hair follicle but also to epidermal cells. Other experiments also have provided new evidence that the upper outer-root sheath of vibrissal (whisker) follicles of adult mice contains multipotent stem cells, which can differentiate into hair follicle matrix cells, sebaceous gland basal cells, and epidermis. Recently, it was reported that multipotent adult stem cells isolated from mammalian skin dermis, termed skin-derived precursors, can proliferate and differentiate in culture to produce neurons, glia, smooth muscle cells, and adipocytes. However, the exact location of these stem cells in skin is unknown, and their functions are still unclear.

The expression of nestin, a marker for neural progenitor cells, in the cells of the follicle bulge, is disclosed herein. Nestin was linked to a fluorescent protein (GFP), which permitted observations of showing that the nestin-containing cells formed the major part of the hair follicle each cycle. This expression of the neural stem cell protein nestin in hair follicle stem cells suggests a possible relation.

Multipotent, nestin-positive, fibronectin-positive stem cells (SKPs) can be generated from juvenile and adult skin, that these precursors derive from the dermis, and that they are distinct from mesenchymal stem cells. Individual clones of SKPs can differentiate into cells of both neuroectodermal and mesodermal lineage, including (but perhaps not limited to) neurons, glia, smooth muscle cells and adipocytes. Studies have shown that SKPs can be passaged for at least 1 year without losing the capacity to generate these diverse cell types. Finally, the human studies indicate that similar precursors may be present within adult human skin. Thus, SKPs apparently represent a novel multipotent adult stem cell that is perhaps less 'biased' than other adult stem cells. The ability to isolate and expand such a stem cell from an accessible, potentially autologous tissue source such as mammalian skin has important therapeutic implications.

These findings identify GATA-3 as a key determinant of the atopic dermatitis (AD). Thus, the nestin-regulated FP transgenic murine model is relevant to the understanding of the physiological significance of the roles of Th2 cells and Th2 cytokines observed in allergic skin diseases such as AD.

Example 5

Nestin-FP Transgenic Mice

Nestin is an intermediate filament (IF) gene that is a marker for CNS progenitor cells and neuroepithelial stem cells. Enhanced GFP (EGFP) transgenic mice carrying EGFP under the control of the nestin second-intron enhancer are used for studying and visualizing the self-renewal and multipotency of CNS stem cells. The work discussed below indicates that hair follicle stem cells strongly express nestin as evidenced by nestin-regulated EGFP expression.

Induction of Anagen

Nestin-regulated GFP transgenic mice, 6-8 weeks old, in the telogen phase of hair growth were depilated by a hot mixture of rosin and beeswax. Samples (5×5 mm$^2$) were excised from the dorsal skin right before depilation (telogen) and at days 1-5 (early anagen), days 8 and 10 (middle anagen), days 14 and 15 (late anagen), and days 19 and 20 (catagen) after depilation. The skin samples were divided into two parts, one for fluorescent microscopy and the other for frozen sections. Briefly, the skin samples were embedded in tissue-freezing embedding medium and frozen at −80° C. overnight. Sections 8 μm thick were cut with a Leica CM1850 cryostat. The frozen sections were air-dried and counterstained with propidium iodide for fluorescent microscopy.

Fluorescent and Confocal Microscopy

The nestin-GFP skin samples, after dissecting out the s.c. tissue, were directly observed with dermis up and epidermis down under a Nikon fluorescent microscope equipped with GFP optics. An MRC-600 confocal imaging system (Bio-Rad) mounted on a Nikon Optiphot with an x10 PlanApo objective was used also.

Immunohistochemical Staining

Colocalization of nestin, keratins 5, 8, and 15, and GFP in the paraffin-embedded C57Bl6 mouse and nestin-GFP transgenic mouse skin sections was detected with the DAKO ARK animal research kit (nestin and keratins) and DAKO EnVision doublestain system following manufacturer instructions. Briefly, the activity of endogenous peroxidase in the skin samples was quenched with incubation in a peroxidase-blocking solution for 5 min. The slide then was incubated with the prepared biotinylated primary antibody (GFP mAb, 1:100; nestin mAb, 1:80; keratin 5/8 mAb, 1:250; and keratin 15 mAb, 1:100) for 15 min followed by incubation with streptavidin peroxidase for 15 min. The staining was completed by incubation with substrate-chromogen 3,3'-diaminobenzidine (DAB) or nuclear fast red for 5 min. Brown (DAB) or cherry-red (nuclear fast red) staining was used for antigen staining. Nestin mAb (rat 401) was purchased from the University of Iowa (Iowa City). Keratin 5/8 mAb (MAB3228) and keratin 15 mAb (CBL 272) were purchased from Chemicon.

The cells with nestin-controlled GFP expression are located in the permanent upper region of telogen hair follicles immediately below the sebaceous glands and in the bulge area. These cells are relatively small, oval- or round-shaped, and interconnected by dendrite-like structures.

The location and number of the nestin-expressing cells is hair-cycle-dependent. The progression and proliferation of the GFP-marked, nestin-producing cells in the developing hair follicle was followed in detail in mice (6-8 weeks old) after inducing anagen in telogen follicles by depilation. As previously described for hair follicle stem cells, at telogen the green fluorescent, nestin-expressing cells in the hair follicle are located only at the upper permanent bulge region. Two to 3 days after depilation, nestin-expressing hair follicle cells have proliferated, migrating down from the bulge. During the middle and late anagen phases, the nestin-expressing hair follicle cells occupy the upper two-thirds of the outer-root sheath and are absent from the lower one-third of the follicle and the hair matrix bulb. In catagen, when hair bulb matrix cells undergo regression and degeneration, the number of outer-root sheath nestin-GFP-expressing cells decreases along with shrinkage of the hair follicle. Eventually, by the next telogen these cells localize only in the bulge.

The data indicate that the nestin-expressing cells include the true progenitor or stem cells of the hair follicle outer-root sheath. At the peak of anagen, fully two-thirds of the length of the follicle outer-root sheath is composed of nestin-expressing GFP-fluorescent cells. These apparently originate in the small cluster of nestin-expressing cells in the telogen follicle and proliferate with kinetics synchronous with the hair cycle. Most of the anagen follicle outer-root sheath must derive from these putative stem cells, because significant recruitment of cells from surrounding tissue seems unlikely in view of the physical, physiological, and temporal barriers. These results provide a depiction of living stem cells forming a critical part the new hair follicle structure.

These results are strongly supported by the findings of others. Recently, Oshima, H., et al., *Cell* (2001) 104: 233-245 reported that the upper region of the outer-root sheath of vibrissal follicles of adult mice contains multipotent stem cells that respond to morphogenic signals to generate multiple hair follicles, sebaceous glands, and epidermis. These findings agree with our observations of nestin-GFP expression in the outer-root sheath.

These nestin-GFP-expressing hair follicle progenitor or stem cells also express keratin 5/8 and keratin 15, which are potential markers of hair follicle stem cells. Results of immunohistochemical staining show that nestin, GFP, and keratins 5/8 and 15 co-localize in the hair follicle bulge cells, outer-root sheath cells, and basal cells of the sebaceous glands.

These data further support the role of nestin-GFP-expressing cells in the hair follicle bulge as the progenitors of the outer-root sheath.

The recent upsurge of interest in hair follicle biology has revealed a surprising complexity of functions and cell types in addition to the obvious role in forming the hair shaft. Here it is reported that the observation that outer-root sheath progenitor cells in the follicle share the nestin marker previously found in neural stem cells. This finding hints at a possible relation between the hair follicle cells and neural stem cells. The data also prove what has previously been suspected, i.e., that the bulge cells that have been shown to express nestin-GFP proliferate to form much of the outer-root sheath during the anagen growth phase. Of course, it is possible that the nestin-expressing cells play a much wider role and serve as stem cells for the entire hair follicle. In this case, the remaining portions of the follicle, e.g., the inner root sheath and the matrix, would originate from the nestin-expressing cells but would lose nestin expression as differentiation proceeded.

Example 6

Isolation of Hair Follicle Stem Cells

Hair follicle bulge nestin-GFP expressing stem cells were isolated and cultured in vitro. Telogen nestin-GFP transgenic mouse skin sample was excised and minced. The minced tissue was then digested with a mixture of trypsin (0.25%), collagenase (0.4%) and dispase (1.0%) at 37° C. for 2 hours. Individual hair follicles with nestin-GFP expressing cells in the bulge area were isolated under a dissection microscope equipped with fluorescence optics. Then the nestin-GFP expressing cells at the bulge area of hair follicle were further isolated with a fine syringe under the fluorescence dissection microscope.

Example 7

B16F10 Murine Melanoma Cells and Nestin Expression

B16F10 murine melanoma cells are shown below to mimic endothelial cell behavior and the angiogenic process in vitro and in vivo. Cord formation in vitro by tumor cells is stimulated by hypoxia and vascular endothelial growth factor (VEGF) and inhibited by antibodies against VEGF and the VEGF KDR receptor (VEGF receptor 2).

The B16F10 murine melanoma cell line (B16F10) are grown in DMEM media 10% FCS, at 37° C. with 5% $CO_2$. The DsRed-2 gene (CLONTECH) is inserted in the retroviral-based mammalian expression vector pLNCX (CLONTECH) to form the pLNCX DsRed-2 vector. Production of retrovirus is performed by transfection of pLNCX DsRed-2 into PT67 packaging cells, which produces retroviral supernatants containing the DsRed-2 gene.

B16F10 cells are cultured in RPMI 1640 medium (GIBCO) containing 15% FCS. 24 hours prior to infection, 70% confluent PT67/RFP cells will be changed to fresh DMEM with 7% FBS medium. The target cells are plated 18 hours before infection, at a cell density of $1-2\times10^5$ per 60 mm plate.

Infected B16F10 cells are transplanted into a host nu/nu mouse and the tumor cells are allowed to grow. Tumor samples are located and excised with samples of normal tissue for fluorescent microscopy. Microscopic images indicate the presence of angiogenic activity by the presence of FP containing blood vessels.

Example 8

Nascent Blood Vessels in the Skin Arise from Nestin-Expressing Hair-Follicle Cells Transgenic mice (ND-GFP) carrying GFP under the control of the nestin second-intron enhancer were used for studying and visualizing the self-renewal and multipotency of CNS stem cells. Hair-follicle stem cells strongly express nestin, as evidenced by nestin-regulated GFP expression.

For the results discussed below, fluorescence microscopy was carried out by using an Olympus IMT-2 inverted microscope (Melville, N.Y.) equipped with a mercury lamp power supply. The microscope had a GFP filter set (Chroma Technology, Rockingham, Vt.). An MRC-600 confocal imaging system (Bio-Rad) mounted on a Nikon Optiphot with a Plan Apo 10X objective was also used to directly observe skin tissue with GFP expression. Immunohistochemical staining for CD31 and von Willebrand factor (VWF) in air-dried skin and frozen sections were performed using the anti-rat Ig horseradish peroxidase (HRP) detection kit (BD Biosciences) for CD31 or anti-rabbit Ig HRP detection kit (BD Biosciences) for VWF, following the manufacturer's instructions. CD31 mAb (CBL1337) was purchased from Chemicon. VWF polyclonal antibody (A0082) was purchased from DAKO. Substrate-chromogen 3,3'-diaminobenzidine staining was used for detection.

Visualization of Nestin Expression in Anagen Mouse Skin

Transgenic ND-GFP mice (6-8 weeks old with almost exclusively telogen (resting) hair follicles) were used to visualize nestin expression in anagen mouse skin. The animals were anesthetized with tribromoethanol (i.p. injection of 0.2 ml per 10 g of body weight of a 1.2% solution). The mice were depilated with a hot mixture of rosin and beeswax to induce anagen. Samples were excised from dorsal skin under anesthesia before depilation and at 48 and 72 h after depilation, when the hair follicles were in early anagen. The skin samples were divided into three parts, one for fluorescence microscopy and the others for frozen sections or air-dried fragments. The samples for frozen sections were embedded in tissue-freezing embedding medium (DAKO) and frozen at −80° C. overnight. Frozen sections 5 μm thick were cut with a CM1850 cryostat (Leica, Deerfield, Ill.) and were air-dried.

FIG. 1 shows views from the dermis side of the doral skin in the ND-GFP transgenic mice. FIG. 1A shows a phase-contrast microscopic image of the dorsal skin from a transgenic animal. The sebaceous glands (downward facing arrows) are located around the hair shaft (upward facing arrows). FIG. 1B shows a phase-contrast microscopic image plus GFP fluorescence. ND-GFP cells are visualized in the follicular bulge area and blood vessels are also seen. The follicular bulge area is located beneath the sebaceous gland. FIG. 1C shows an image of GFP fluorescence. The ND-GFP blood vessels are seen as connected to ND-GFP hair follicles. FIG. 1D shows a schematic of telogen hair follicle showing position of ND-GFP hair-follicle bulge areas and blood vessel network. FIG. 1E also shows an image of GFP fluorescence. The ND-GFP blood vessels are seen as being associated with ND-GFP hair-follicle bulge areas. Scale bars in the figures represent a distance of 100 μm.

As seen in FIG. 1A-D, the nestin-expressing hair follicles are interconnected by an ND-GFP-labeled dermal vascular network. Immunohistochemical staining showed that the network vessels display CD31 antigen and VWF, indicating that they are blood vessels.

Transplantation of ND-GFP Vibrissa Follicles to Nude-Mouse Wounded Skin

For transplantation purposes, vibrissa follicles from ND-GFP transgenic mice were surgically obtained. The transgenic mice were anesthetized and all surgical procedures were carried out in a sterile environment. The upper lip containing the vibrissal pad was cut, and its inner surface was exposed. The follicles were dissected under a binocular microscope and plucked from the pad by pulling them gently by the neck with fine forceps. All follicles were then kept in DMEM/F-12 medium containing B-27 supplement (GIBCO/BRL).

Recipient nude mice were anesthetized with tribromoethanol as described above. A sample of full-thickness skin was folded and two neighboring full-thickness wounds ~15 mm apart were made with a 2-mm biopsy punch. ND-GFP vibrissa follicles were then transplanted. The incision was closed with nylon sutures (6-0). Samples of subcutis of the transplanted mice were subsequently excised and directly observed by fluorescence microscopy and air-dried or prepared for frozen sections for immunohistochemical staining. The mice were anesthetized and wounded skin samples were excised at day 10 after wounding for analysis.

FIG. 2A-G shows images of ND-GFP vibrissa follicles transplanted into the subcutis of a nude mouse. FIG. 2A shows a phase-contrast micrograph of a follicle 28 days after transplantation. Pre-existing blood vessels are shown at the bottom of the image. FIG. 2B shows the same follicle as a phase-contrast micrograph plus GFP fluorescence. Nestin-positive blood vessels are shown connected to pre-existing blood vessels in this image. FIG. 2C shows an image of GFP fluorescence of the transplanted follicle. In FIGS. 2B and 2C, ND-GFP blood vessels are seen growing from the transplanted ND-GFP hair follicle and associating with preexisting blood vessels in the nude-mouse skin. FIGS. 2D and 2E show higher magnification images of from the ND-GFP vessels of FIGS. 2B and 2C, respectively. (f and g) FIGS. 2F and 2G show images of GFP signals and the endothelial cell marker CD31, colocalized. FIG. 2F is a fluorescent image, and FIG. 2G shows the same field air-dried and immunohistochemically stained with CD31. (Scale bars, 100 μm.)

ND-GFP vessels were detected growing from the transplanted ND-GFP hair follicle in nude-mouse skin by day 3. As discussed in regards to FIG. 2 above, by day 28, the nestin-GFP-expressing vessels had developed into an extensively branched network and appeared to anastomose with existing vessels in the recipient nude mice. Immunohistochemical staining showed that CD31 antigen and GFP fluorescence colocalized in nascent vessels.

Transplantation of ND-GFP Vibrissa Follicles Under the Kidney Capsule of Nude Mice Vibrissa follicles were harvested as described above. All follicles were then kept on ice in DMEM/F-12 medium containing B-27 supplement until they were transplanted underneath the kidney capsule of 6- to 8-week-old nu/nu mice, which were anesthetized as described above. An incision was made on the left flank of the recipient mouse, and the kidney was exposed. Two follicles were inserted beneath the kidney capsule. The kidney was then brought back into place, and the incision was closed with nylon sutures (6-0). On day 14 the kidney capsule of each transplant mouse was excised and directly observed by fluorescence microscopy.

FIG. 3A-C show images of transplanted ND-GFP vibrissa follicles under the kidney capsule of a nude mouse. The ND-GFP vessels were visualized to form a network at day 14 after transplantation, as seen phase-contrast micrograph (FIG. 3A), phase-contrast micrograph plus GFP fluorescence (FIG. 3B), and GFP fluorescence (FIG. 3C). (Scale bars, 100 µm.) The ND-GFP vessels appeared to anastomose with preexisting blood vessels.

After transplantation of ND-GFP vibrissa follicles under the kidney capsule in a nude mouse, an ND-GFP blood vessel network around the transplanted follicles was observed on day 14 (FIG. 3). The ND-GFP vessels appeared to anastomose with preexisting blood vessels.

Figure 4E:
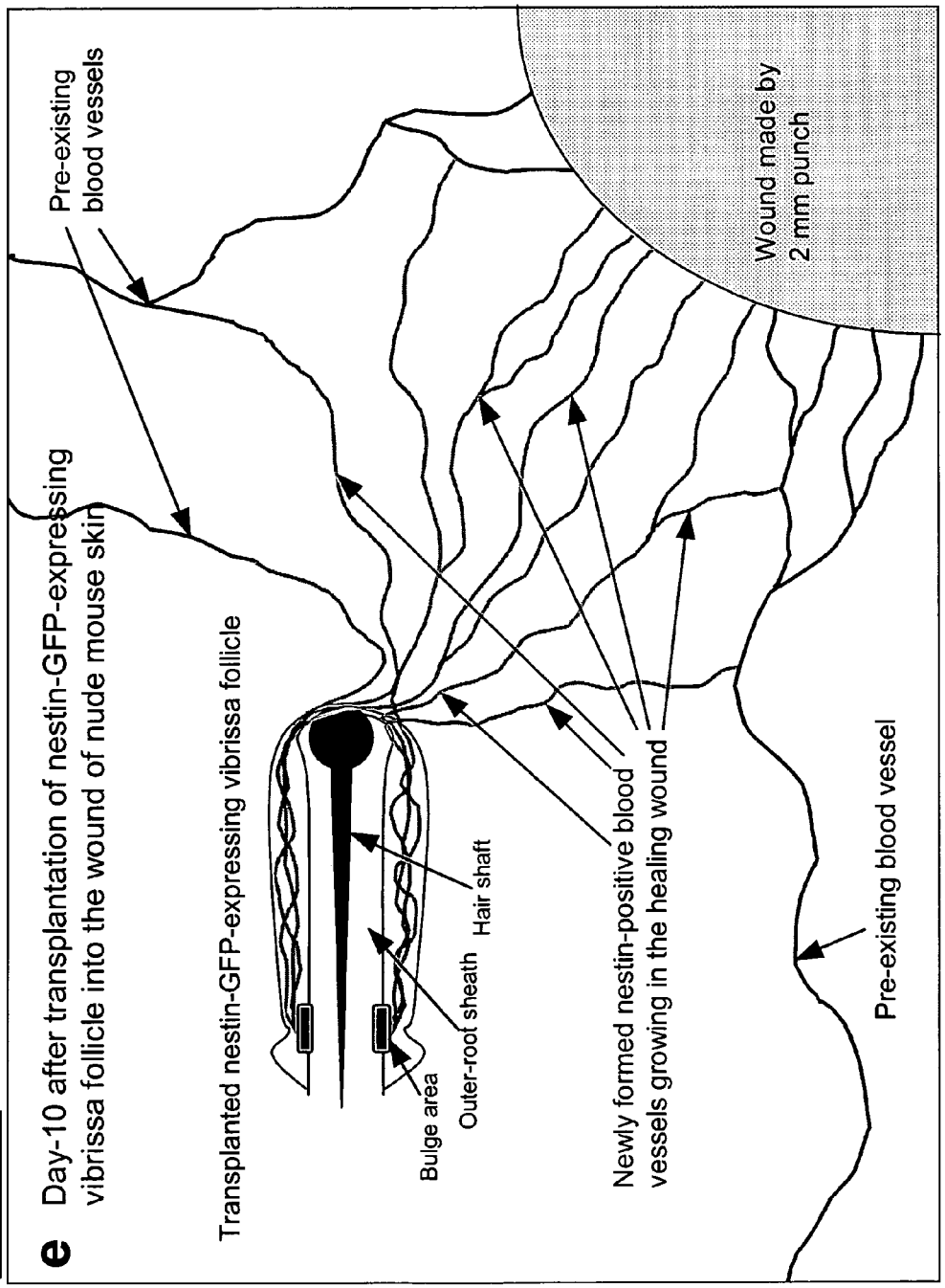

Enhanced Growth of ND-GFP Vessels from Transplanted Hair Follicles in Wounded Skin Wounded skin samples containing transplanted ND-GFP vibrissa hair follicles were harvested for fluorescence microscopy. FIG. 4A shows an isolated ND-GFP vibrissa follicle before transplantation. FIG. 4B shows an image of the ND-GFP vibrissa follicle into wounded nude-mouse skin 10 days after transplantation. The ND-GFP vessels were seen growing from the ND-GFP vibrissa follicle toward the healing wound. FIGS. 4C and D show higher magnification of the area in FIG. 4B, as indicated by the white dashed box. FIG. 4E schematic of transplantation of the ND-GFP vibrissa follicle into wounded nude-mouse skin. (Scale bars, 100 µm.)

The images of FIG. 4 show that ND-GFP vessels grew from the hair follicles toward the wound. The presence of a wound in the vicinity of the transplanted follicle significantly enhanced vessel outgrowth. Apparently, vessels originating in the follicle responded to angiogenic signals arising from the wound vicinity. Immunohistochemical staining showed that CD31 was expressed in the ND-GFP-expressing vessels growing into the wound.

Discussion

Angiogenesis, the highly active growth and destruction of capillary blood vessels, has come to occupy an increasingly important role in understanding tissue maintenance, wound repair, and the growth of malignancies. Identifying the source of the cells for new blood vessels has become increasingly important both scientifically and for therapeutic design. There have been numerous recent reports of endothelial cells arising from bone marrow-derived stem cells. There is also evidence that endothelial stem cells can be derived from adipose tissue. However, these previously identified sources of endothelial stem cells may not be able to supply blood vessels in the skin because of skin's unique structure. The results provided above indicate that an important and previously unrecognized function of hair-follicle stem cells is to supply endothelial cells that can form blood vessels in the skin.

The repertoire of hair-follicle stem cell potential may be even broader than reported here. A number of investigators found that multipotent adult stem cells isolated from mammalian skin dermis, termed skin-derived precursors, can proliferate and differentiate in culture to produce neurons, glia, smooth muscle cells, and adipocytes. However, the exact location of these stem cells in skin was unknown, and their functions were unclear. The present report suggests that the hair follicle is an important source of stem cells for dermal blood vessels and very likely for other tissues as well. These results support reports that follicle cells contribute to wound repair as well as to skin transplant survival.

Example 9

Angiogenesis Model to Screen an Angiogenesis Promoting Compound

For transplantation purposes, vibrissa follicles from ND-GFP transgenic mice is surgically obtained as discussed in Example 8. All follicles are then kept in DMEM/F-12 medium containing B-27 supplement (GIBCO/BRL).

Recipient nude mice are anesthetized, and a sample of full-thickness skin is folded and two neighboring full-thickness wounds ~15 mm apart are made with a 2-mm biopsy punch. ND-GFP vibrissa follicles are then transplanted. The incision is closed with nylon sutures (6-0).

The mice are divided into an experimental group and a control group. The experimental group received a treatment series comprising vascular endothelial growth factor, a known angiogenesis promoting compound in a pharmaceutically acceptable carrier. The control group of mice receives only the carrier.

Following treatment, samples of subcutis of the transplanted mice are subsequently excised and directly observed by fluorescence microscopy and air-dried or prepared for frozen sections for immunohistochemical staining. The extent of angiogenic activity in the samples taken from the experimental and control groups. Samples taken from the experimental group indicate an higher degree of angiogenic activity based on the amount of GFP activity as compared to that seen in the control samples.

This example indicates that the disclosed model system has utility as a screen for angiogenic agents.

Example 10

Angiogenesis Model to Screen an Angiogenesis Inhibiting Compound

For transplantation purposes, vibrissa follicles from ND-GFP transgenic mice is surgically obtained as discussed in Example 8. All follicles are then kept in DMEM/F-12 medium containing B-27 supplement (GIBCO/BRL).

Recipient nude mice are anesthetized, and a sample of full-thickness skin is folded and two neighboring full-thickness wounds ~15 mm apart are made with a 2-mm biopsy punch. ND-GFP vibrissa follicles are then transplanted. The incision is closed with nylon sutures (6-0).

The mice are divided into an experimental group and a control group. The experimental group received a treatment series comprising vasoinhibin, a known angiogenesis inhibiting compound in a pharmaceutically acceptable carrier. The control group of mice receives only the carrier.

Following treatment, samples of subcutis of the transplanted mice are subsequently excised and directly observed by fluorescence microscopy and air-dried or prepared for frozen sections for immunohistochemical staining. The extent of angiogenic activity in the samples taken from the experimental and control groups. Samples taken from the experimental group indicate a reduced degree of angiogenic activity based on the amount of GFP activity as compared to that seen in the control samples.

This example indicates that the disclosed model system has utility as a screen for anti-angiogenic agents.

Example 11

Transplantation of FP-Expressing Hair Follicle Cells into a FP-Transgenic Host

ND-GFP-expressing vibrissa hair follicle cells are prepared in a transgenic mouse. A transgenic host organism, a nu/nu mouse is engineered to express RFP under nestin regulatory control (ND-RFP). ND-GFP-expressing vibrissa hair follicle cells are transplanted into skin wounds made in the ND-RFP-transgenic host organism, as discussed in Example 8.

Wounded skin samples containing transplanted ND-GFP vibrissa hair follicles are harvested for fluorescence microscopy. An isolated ND-GFP vibrissa follicle is subjected to microscopy before transplantation. An image of the ND-GFP vibrissa follicle into wounded nu/nu ND-RFP mouse skin 10 days after transplantation. The ND-GFP vessels are seen growing from the ND-GFP vibrissa follicle toward the healing wound. ND-RFP vessels projecting from the wound are also seen.

Example 12

Growing Stem Cells

The nestin-GFP expressing cells from the bulge area of hair follicle were transferred to M21 media without growth factor supplements, which is the typical neural maintenance media to grow neurospheres (Uchida, N., et al., *Proc. Natl. Acad. Sci. USA* (2000) 97:14720-14725). After 12 days, neurosphere-like colonies were apparent. In another experiment, isolated nestin-GFP expressing cells from the hair follicle bulge area were grown at 10 cells/mm$^2$ in methylcellulose (1.2%) containing neural stem cell culture media supplemented with epidermal growth factor (EGF) (20 ng/ml), fibroblast growth factor (FGF) (20 ng/ml) and leukemia inhibitory factor (Lif) (10 ng/ml) every two days. When spheres were apparent in the culture medium, they were transferred to a new plate without methylcellulose. Secondary spheres were also generated from the primary spheres. Spheres were then assayed for their differentiation potential.

The invention claimed is:

1. A method of monitoring blood vessel development in vivo, comprising:
    providing a mouse hair follicle stem cell isolated from vibrissa follicles, wherein the stem cell comprises an expression cassette encoding a first fluorescent protein (FP) under control of a hair follicle tissue specific promoter and the nestin second-intron enhancer and wherein the stem cell is a nestin expressing cell;
    growing the stem cell in an allogeneic immunodeficient mouse host; and
    visualizing nascent blood vessel development produced by the stem cell following growth of the stem cell, whereby blood vessel development is monitored.

2. The method of claim 1, wherein the fluorescent protein is selected from the group consisting of green fluorescent protein (GFP), red fluorescent protein (RFP), blue fluorescent protein (BFP) and yellow fluorescent protein (YFP).

3. The method of claim 1, wherein the host is a nude mouse.

4. The method of claim 1, wherein the stem cell an angiogenic stem cell.

5. A method of screening for a modulator of nascent blood vessel development in vivo, comprising:
    providing a mouse hair follicle stem cell isolated from vibrissa follicles, wherein the stem cell comprises an expression cassette encoding a first fluorescent protein (FP) under control of a hair follicle tissue specific promoter and the nestin second-intron enhancer and wherein the stem cell is a nestin expressing cell;
    growing the stem cell in an allogeneic immunodeficient mouse host in the presence of an exogenously added angiogenesis modulating agent; and
    visualizing nascent blood vessel development produced by the stem cell growth of the stem cell.

6. The method of claim 5, wherein the fluorescent protein is selected from the group consisting of green fluorescent protein (GFP), red fluorescent protein (RFP), blue fluorescent protein (BFP) and yellow fluorescent protein (YFP).

7. The method of claim 5, wherein the host is a nude mouse.

8. The method of claim 5, wherein the stem cell is an angiogenic stem cell.

9. The method of claim 1, wherein the stem cell further comprises a second FP protein under control of the nestin second-intron enhancer, wherein the first FP protein is different from the second FP protein.

10. The method of claim 8, wherein the host organism comprises a second FP protein under control of the nestin second-intron enhancer, wherein the first FP protein is different from the second FP protein.

* * * * *